US008488857B2

(12) United States Patent
Young et al.

(10) Patent No.: US 8,488,857 B2
(45) Date of Patent: Jul. 16, 2013

(54) AUTOMATED DIAGNOSIS AND ALIGNMENT SUPPLEMENTED WITH POSITRON EMISSION TOMOGRAPHY (PET) AND MAGNETIC RESONANCE (MR) FLOW ESTIMATION

(75) Inventors: Stewart M. Young, Hamburg (DE); Michael Kuhn, Hamburg (DE); Fabian Wenzel, Hamburg (DE); Ingwer C. Carlsen, Hamburg (DE); Kirsten Meetz, Hamburg (DE); Ralph Buchert, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 755 days.

(21) Appl. No.: 12/529,195

(22) PCT Filed: Feb. 14, 2008

(86) PCT No.: PCT/IB2008/050545
§ 371 (c)(1),
(2), (4) Date: Feb. 25, 2010

(87) PCT Pub. No.: WO2008/107809
PCT Pub. Date: Sep. 12, 2008

(65) Prior Publication Data
US 2010/0152577 A1 Jun. 17, 2010

Related U.S. Application Data (60) Provisional application No. 60/893,241, filed on Mar. 6, 2007.

(51) Int. Cl.
*G06K 9/00* (2006.01)
*G06K 9/62* (2006.01)
*A61B 5/02* (2006.01)

(52) U.S. Cl.
USPC .................. 382/131; 362/209; 600/504

(58) Field of Classification Search
USPC ........................................... 382/131
See application file for complete search history.

(56) References Cited

U.S. PATENT DOCUMENTS 3,890,959 A   6/1975   Youdin et al.
7,433,540 B1 * 10/2008   Schuster .................. 382/284

(Continued)

FOREIGN PATENT DOCUMENTS

JP   2006167289 A   6/2006
WO      9317352 A1   9/1993

(Continued)

OTHER PUBLICATIONS

Kawachi et al., Comparison of the diagnostic performance of FDG-PET and VBM-MRI in very mild Alzheimer's disease, European Journal of Nuclear Medicine and Molecular Imaging, vol. 33, No. 7, pp. 801-809, Jul. 2006.*

(Continued)

*Primary Examiner* — David Zarka (57) ABSTRACT

A scanner (10) is used to provide images for automated diagnoses of neurodegenerative diseases, such as Alzheimers disease. The images are registered (90) to a template (78). The aligned image is analyzed (60) in relation to reference image data (76, 80) which has been registered to the template which is contained in a knowledge maintenance engine (70) for similar patterns of hypo-intensity that would indicate (in the case of an FDG tracer) reduced glucose uptake in the brain. The most appropriate reference images for the analysis of the present study are chosen by a filter (74). The present study is then given a dementia score (84) as a diagnostic feature vector that indicates to a clinician the type and severity of the ailment based on the analysis. The scanner (10) can produce PET or other metabolic and MR images for diagnosis. The MR can be used to measure blood flow rate into the brain. From the blood flow rate and the metabolic image, tracer, e.g. FDG, uptake maps can be generated for use in the automated diagnoses.

22 Claims, 4 Drawing Sheets

U.S. PATENT DOCUMENTS

| | | | |
|---|---|---|---|
| 2005/0273007 A1* | 12/2005 | Burbar | 600/436 |
| 2006/0030769 A1 | 2/2006 | Ramamurthy et al. | |
| 2006/0120584 A1* | 6/2006 | Hillman | 382/128 |
| 2006/0251312 A1 | 11/2006 | Krieg et al. | |
| 2008/0091118 A1* | 4/2008 | Georgopoulos | 600/544 |
| 2009/0181911 A1* | 7/2009 | Zlokovic et al. | 514/44 |
| 2011/0082187 A1* | 4/2011 | Campbell et al. | 514/44 A |
| 2011/0286650 A1* | 11/2011 | Roy et al. | 382/131 |

FOREIGN PATENT DOCUMENTS

| | | |
|---|---|---|
| WO | 2006009752 A1 | 1/2006 |
| WO | 2006119085 A2 | 11/2006 |

OTHER PUBLICATIONS

Ishii, K., et al.; Fully automatic diagnostic system for early-and late-onset mild Alzheimer's disease using FDG PET and 3D-SSP; 2006; European J. of Nuclear Medicine and Molecular Imaging; 33(5)575-583.

Matsuda, H., et al.; Conversion of brain SPECT images between different collimators and reconstruction processes for analysis using statistical parametric mapping; 2004; Nuclear Medicine Communications;25:67-74.

Patlak, et al., "Graphical Evaluation of Blood-to-Brain Transfer Constants from Multiple-Time Uptake Data", Journal of Cerebral Blood Flow and Metabolism, 3:1-7 (c)1983 Raven Press, NY.

Shao, et al., "Development of a PET Detector System Compatible with MRI/NMR Systems", IEEE Transactions on Nuclear Science, vol. 44, No. 3, Jun. 1997 (c) 1997 IEEE; pp. 1167-1171.

Marsden, et al., "Simultaneous PET and NMR", The British Journal of Radiology, 75 (2002) S53-S59, (c) 2002 the British Institute of Radiology.

Herholz, et al., "NeuroPET PET in Neuroscience and Clinical Neurology", Springer Pub., Chapter 4.9.1.5-Chapter 4.10, pp. 212-223, ISBN 3-540-00691-5, springeronline.com; 2004.

Kiebel, et al., "MRI and PET Coregistration-A Cross Validation of Statistical Parametric Mapping and Automated Image Registration", Neuroimage 5, 271-279 (1997) Article No. N1970265 (c) 1997 Academic Press.

Friston, et al., "Spatial Registration and Normalization of Images", The Wellcome Dept. of Cognitive Neurology, The Institute of Neurology, Queen Square UK and the MRC Cyclotron Unit, DuCane Road, London, UK, Hammersmiith Hospital, (c) 2004 Society of Photo-Optical Instrumentation Engineers, Publ. in Proc. of SPIE vol. 5370 Human Brain Mapping 2:165-189 (1995).

Kabus, et al., "B-Spline Registration of 3D Images with Levenberg-Marquardt Optimization", Institute of Mathematics, University of Luebeck, Luebeck, Germany; Proc. SPIE 5370; Medical Imaging 2004: Imapge Processing 304 (May 12, 2004); doi:10.1117/12.533976.

Buchert, et al., "Adjusted Scaling of FDG Positron Emission Tomography Images for Statistical Evaluation in Patients with Suspected Alzheimer's Disease", (c) 2005 American Society of Neuroimaging, Accepted for publication May 24, 2005 pp. 348-355.

Minoshima, et al., "A Diagnostic Approach in Alzheimer's Disease Using Three-Dimensional Stereotactic Surface Projections of Fluorine-18-FDG PET", The Journal of Nuclear Medicine, vol. 36, No. 7, Jul. 1995, pp. 1238-1248.

Young, et al., "Automated Planning of MRI Neuro Scans", Philips Research Laboratories, Hamburg, Germany; Medical Imaging 2006: Image Processing. Edited by Reinhardt, Jospeh M.; Pluim, Josien P. W. Proceedings of the SPIE, vol. 6144, pp. 551-558 (2006).

* cited by examiner

AUTOMATED DIAGNOSIS AND ALIGNMENT SUPPLEMENTED WITH POSITRON EMISSION TOMOGRAPHY (PET) AND MAGNETIC RESONANCE (MR) FLOW ESTIMATION

CROSS REFERENCE TO RELATED APPLICATIONS

This application claims the benefit of U.S. provisional application serial no. 60/893,241 filed Mar. 6, 2007, which is incorporated herein by reference.

The present application relates to the diagnostic imaging arts. It finds particular application in early diagnosis of dementia and will be described with particular attention thereto. Aspects will have numerous other applications.

Dementia affects more than 30 million people worldwide, and incidence rates are rising as the average age of the population in more affluent nations increases. Alzheimer's disease is the most common cause of dementia, and although no effective long term treatment is yet available, treatments are available that can slow the onset of dementia if the underlying cause is diagnosed early. Providing an accurate and timely diagnosis for patients exhibiting clinical symptoms of dementia is of the utmost importance in order to initiate appropriate pharmacotherapy, which is most likely to be effective when initiated soon after onset. A reliable diagnostic approach could potentially pave the way for screening programs to detect dementia before the onset of clinical symptoms, especially in subjects with mild cognitive impairment.

Neuro-imaging offers a diagnostic alternative to waiting for the manifestation of clinical symptoms. For both early and differential diagnosis, PET imaging using a glucose based tracer provides a promising biomarker for neurodegenerative disease. Tracer uptake patterns reveal regions exhibiting reduced brain glucose metabolism. This enables clinicians to distinguish between alternative underlying causes of dementia, with different illness types yielding distinct and characteristic patterns of reduced glucose metabolism. An alternative approach is to use MRI based measurements of volume changes over time in the medial temporal lobe of the brain. These arise due to neuronal atrophy in the hippocampus, and have been demonstrated to provide a sensitive biomarker for progression of Alzheimer's disease. A solely MR based approach, however, requires a longitudinal study to establish morphological changes, and is furthermore specific to a single cause of dementia (Alzheimer's disease). Hippocampal volume changes are very localized, with more widespread cortical atrophy effects visible only in later stages of the disease.

Approaches for the evaluation of functional imaging studies of the brain typically follow a scheme that first aligns an image of the brain of the patient with a template image in a non-linear fashion. This is often called stereotactic normalization since the template is pre-aligned within a known stereotactic space such as the Talairach atlas. The image intensities in the spatially normalized patient image are then statistically compared to a set of images of asymptomatic patients, in order to generate a parameter map of regions exhibiting hypo-intensity, and assumedly, reduced metabolic uptake of glucose. Optionally, the global intensity level of the patient image can be normalized to allow for the fact that absolute levels of tracer uptake vary greatly from subject to subject. This can be compensated for by estimation of a global scaling factor by which all image voxels are multiplied before statistical comparison.

An important application of PET in neuro-imaging involves measuring regional cerebral metabolic rate of glucose to identify individuals suffering from neurodegenerative diseases, such as Alzheimer's disease and other dementias, by observing characteristic patterns of hypo-metabolism in specific regions of the neo-cortex. Regions of hypo-metabolism can be identified by comparing the individual PET image to a reference population of healthy subjects in order to devise a parametric map indicating regions in which the observed intensity deviates significantly from the normal population. This requires that the images first be spatially aligned and then normalized in intensity levels. Intensity normalization requires the definition of a global scaling factor, which is applied to all image voxels to adjust image intensities to match the normal population.

Spatial alignment is a critical step in the automated evaluation of functional images of the brain, such as fluorodeoxyglucose (FDG) PET data for evaluation of dementia patients. The aim is to identify brain regions exhibiting hypo-intensity, indicating (in the case of an FDG tracer) a reduced rate of glucose metabolism and thus pathologically affected brain tissue. The spatial distribution of the affected regions is characteristic of the underlying cause of dementias, and is an important biomarker for the differential diagnosis of diseases such as Alzheimer's disease and fronto-temporal dementia.

For automated evaluation of functional neuro-images, a patient image should first be elastically registered with a template PET image, which defines a common reference frame. These images are aligned to an atlas image such as a Talairach atlas image. Next, the global intensity level is normalized, since the variations in imaging protocol and metabolism rate between patients can cause significant variations in the absolute tracer uptake in the brain. Finally, a voxel-wise statistical comparison is performed between intensities in patient and asymptomatic collective images, and hypo-intensity is detected at some pre-defined significance level. The normal collective images provide a model of the variability present within the healthy population. The model is specific to a range of factors including the patient protocol and the imaging system. The statistical comparison yields a statistical parameter map, which is interpreted visually for diagnostic purposes.

Alignment is important in the evaluation of the images, and is also used for alignment of patient data to the template image, registration of images to each other within the healthy population sample, and for spatial normalization of the template with the healthy population sample. Resultantly, the accuracy of this alignment is of paramount importance, since it is directly linked to the validity of the evaluation. Inaccurate alignment of images in the healthy patient sample can, for example, induce higher standard deviation in the model, and leads directly to reduced sensitivity of the statistical test. Spatial alignment of two PET images is realized using elastic registration methods that optimize the parameters of fitting, and due to computational efficiency constraints, the dimensionality of the adopted non-linear transformation is generally constrained.

An alternative approach for spatial alignment which has been proposed is to perform an intra-patient, inter-modality rigid registration between a PET and an MR image of the patient, followed by an elastic registration of the MR image with an MR template image (which is already previously aligned with the PET template). The two resulting transformations can then be concatenated and applied to the patient's PET image to derive a stereotactically normalized patient PET image.

There are at least two practical limitations of a registration based approach to image alignment. One is the complexity of the elastic transformation model. This is typically limited, in practice, by constraining the degrees of freedom in the adopted transformation model, for example, if a spline-based interpolation model is assumed then by adopting a limited number of spline control points. This means that although broad shape variations can be compensated, structural variability with high spatial frequency may not be compensated. A prominent example is the shape of the ventricle cavity, which has a very high inter-subject shape variability, as well as a high contrast between cerebral-spinal fluid in the cavity and the surrounding brain tissue. Limited complexity of the elastic registration leads to high residual variance within populations of spatially aligned images. Another problem can arise when trying to estimate the rigid transformation between PET and MR images. A "skull-stripping' pre-processing step can be utilized, since the skull structure is not present in a PET image and can thus destabilize a rigid registration between a PET image and an MR image.

Flow estimation is a difficult prospect when analyzing a PET image, and it is often advantageous to use the superior flow estimation characteristics of an MR image to enhance the value of the data gleaned from a PET image. Despite well-known technical challenges concerning the operation of PET detectors within close proximity to an MR scanner, there has been a long standing desire to create a combined PET/MR imaging device. Recent developments in PET detector technology have lead to the possibility of realizing such a scanner in the near future, perhaps starting with application specific scanner designs, (e.g. head only) and improving to more general imaging systems. Since PET detectors typically utilize electron cascade photomultiplier tubes, the strong $B_0$ field of an MR scanner can disrupt these detectors, which utilize charged particles. One solution to this dilemma is presented in co-pending provisional application No. 60/884, 486 filed on Jan. 11, 2007, assigned to Philips Medical systems. Another possible solution is to use a PET detector that utilizes solid state detector elements instead of the more typical photomultiplier tubes. Another solution is to move the patient, e.g. with the patient support, between MR and PET imaging areas Applications in neuro-imaging would also benefit particularly from a combination of functional imaging (both via PET and, using the BOLD effect in fMRI) and MR anatomical imaging. For example, a correlation of PET and MR data would better enable localization of epileptic foci.

In PET imaging, the image is created by detecting decay of radioactive isotopes that are attached to biochemical tracers. PET imaging of the brain yields localized, time resolved measurements of the uptake of the applied tracer. In order to quantitatively estimate parameters of the underlying physiological processes, however, a model is required to describe the transport of the tracer from the blood plasma into the imaged tissue. The fitting of such models to PET data typically requires estimates of the arterial blood flow rate and tracer concentration, referred to as the 'input function.' The most accurate method of obtaining such a measurement is direct sampling of the arterial blood. This is an invasive approach that entails significant inconvenience for the patient, so it is desirable to conceive more comfortable alternatives.

By measuring the arterial blood flow, a clinician can determine the concentration of tracer entering the brain at known time points, and then compare those values to resultant images. In order to avoid the invasive process of sampling the patient's arterial blood, post processing methods have been typically adopted, for example using a scale factor defined using the mean intensities within a pre-imaged sampling of the healthy population. This method, however, is generally sub-optimal and can lead to artifacts in derived parametric maps.

DESCRIPTION

In accordance with one aspect, a method of automated diagnosis using a positron emission tomography scanner is provided. A diagnostic image of a region of interest is produced. A knowledge maintenance engine is consulted for data from past imaging scans and diagnoses. The diagnostic image is analyzed, identifying areas of the image that appear different from images taken of an asymptomatic control collective.

In accordance with another aspect, a positron emission scanning apparatus is presented. An imaging portion generates a positron emission tomography image of a portion of a subject. An image memory stores a reconstructed positron emission tomography image. An analysis processor analyzes the positron emission tomography image and assigns a score indicative of a diagnosis. A knowledge maintenance engine provides previously gathered data to the analysis processor to aid the analysis processor in its analysis. A filter (74) limits information from the knowledge maintenance engine to information that is most pertinent to a present study.

In accordance with another aspect, a method of diagnostic image registration is provided. A first diagnostic image of a region of interest is produced. A second diagnostic image of the region of interest is also produced. The first and second diagnostic images are aligned with respect to the structures present in the images.

In accordance with another aspect, a method of diagnostic imaging is provided. A first diagnostic image of a region of interest is produced with a first image modality. A second diagnostic image of the region of interest is produced with a second image modality, the second modality being different than the first modality. The first and second diagnostic images are aligned. A medical abnormality appearing in at least one of the first and second diagnostic images is then diagnosed.

In accordance with another aspect, a dual modality scanning apparatus is provided. A magnetic resonance imaging portion of the apparatus is capable of generating a magnetic resonance image of at least a portion of a subject in an imaging region. A magnetic resonance image memory stores a reconstructed magnetic resonance image. A positron emission tomography portion of the apparatus is capable of generating a positron emission tomography image of the portion of the subject. A positron emission tomography image memory stores a reconstructed positron emission tomography image. An image registration processor registers and combines the magnetic resonance image and the positron emission tomography image, forming a pair of co-registered images. An image memory stores the co-registered images. An analysis processor analyzes the co-registered images and assigns a feature vector indicative of a diagnosis. A knowledge maintenance engine provides previously gathered data to the analysis processor to aid the analysis processor in its analysis. A filter limits information from the knowledge maintenance engine to information that is most pertinent to a present study.

In accordance with another aspect, a diagnostic imaging apparatus is provided. An image construction portion generates a diagnostic image of a portion of a subject. An image memory stores a plurality of reconstructed images. An image registration processor registers and combines at least two images from the image memory, forming a pair of co-registered images. A co-registration image memory stores the co-registered images.

In accordance with another aspect, a method of determining an amount of tracer uptake in a region of interest of a subject is provided. A radioisotope tagged with a tracer is injected into a subject. A first diagnostic image of a region of interest is produced with a first image modality. A second diagnostic image of the region of interest is produced with a second image modality, the second modality being different than the first modality. From the first diagnostic image, an amount of blood inflow into the region of interest is determined with a magnetic resonance scanner. An amount of tracer uptake in the region of interest is calculated.

In accordance with another aspect, a dual modality scanning apparatus is provided. A magnetic resonance imaging portion generates a magnetic resonance image of at least a portion of a subject in an imaging region. A magnetic resonance image memory stores a reconstructed magnetic resonance image. A positron emission tomography portion generates a positron emission tomography image of the portion of the subject. A positron emission tomography image memory stories a reconstructed positron emission tomography image. An uptake processor calculates an amount of tracer uptake in the portion of the subject by applying the relationship $$\frac{C_t(t)}{C_a(t)} = k_i \frac{\int_0^t C_a(\tau) d\tau}{C_a(t)} + B$$

where $C_t(t)$ is a tissue concentration, $C_a(t)$ is an arterial concentration, k, is an influx constant, and B represents a free tracer component.

One advantage lies in automated differential diagnosis and classification of patterns of hypo-intensity.

Another advantage lies in enhanced accuracy of sterotactical normalization.

Another advantage lies in increased consistency in outcomes, even if aspects of the imaging processes or hardware components are changed.

Another advantage lies in improved alignment of neuro images across subjects.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The application now turns to description of several exemplary embodiments. While the application includes description of a combined PET/MR scanner, it is to be understood that automated diagnosis techniques and landmark based spatial alignment are not dependent on a multimodality system, but merely enhanced thereby. The application first discusses automated diagnosis using PET imaging, and then landmark based spatial alignment of PET images. Both of these concepts can be enhanced with concurrent MR imaging data, but the MR data is not necessary. The application then turns to scaling of intensity values from PET image to PET image, using the benefits of MR flow measurement. The application then lays the groundwork for a multimodality environment.

Figure 1:
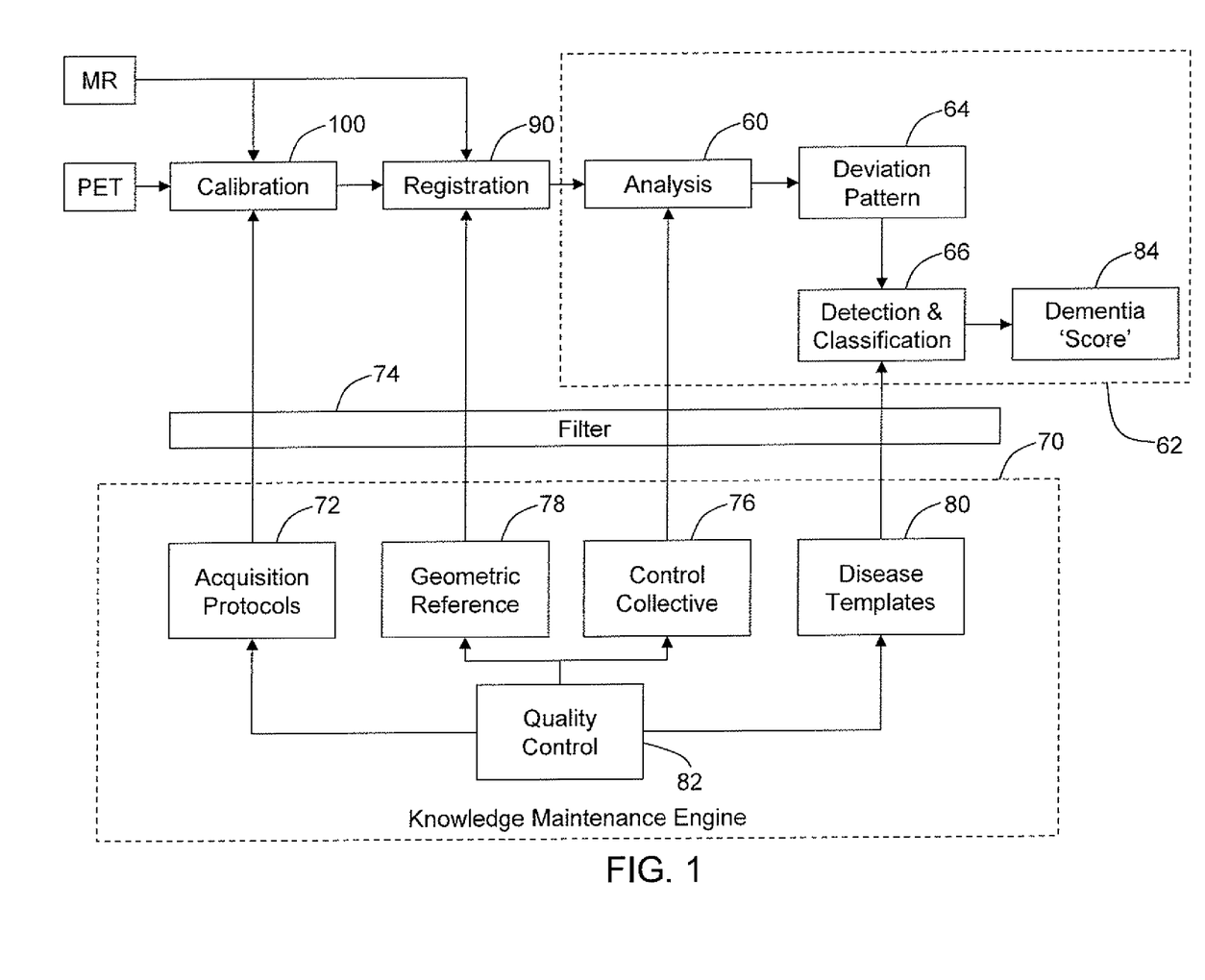
FIG. 1 is a flow diagram of steps that a scanner proceeds through to create an automated diagnosis.

A PET or other diagnostic image alone can be used to automatically diagnose medical ailments. Again, the present embodiment is described with reference to diagnosing degenerative neurological diseases, but it is to be understood that the nature of the PET imaging modality can be used in conjunction with myriad other diagnoses. With reference now to FIG. 1, a system for automated evaluation of dementia is illustrated. An analysis 60 of the PET image data is performed with a data analysis processor 62. Another possibility is that single photon emission computed tomography (SPECT) image data can be used in place of the PET image data. Significant deviations between the calibrated physiological input data and an asymptomatic collective are detected. The system 10 notes the deviations in step 64 and classifies the ailment in step 66. Standard statistical tests, e.g. the test currently used serve as straightforward implementation. The result of such a comparison is a data set giving for each location in the field of view a difference measure indicative of the deviation between the tracer uptake at that particular location in the patient data and the corresponding location in the control collective. The spatial distribution of these deviations is (in the case of an FDG tracer) characteristic of the type of dementia.

The spatial distribution of areas of significant hypo-intensity (low glucose uptake for an FDG tracer) is compared to a set of models representing disease specific patterns. The set of models may be derived from group based testing of patients with confirmed diagnoses, with respect to the healthy reference collective. The comparison of these models to the patterns derived from the current patient provides a quantitative basis on which to perform a fully automated differential diagnosis. This step enables a completely computer assisted diagnosis of the input patient image data.

As a basis of the automatic diagnosis, the system uses several knowledge sources that are all a part of a collective knowledge maintenance engine 70. The knowledge maintenance engine 70 can be, for example, a hospital wide database or a larger scale, as in a multi-hospital network database, or further, a publicly accessible information database. Although it is advantageous to have scanner specific data, it is also advantageous to have as much clinical data as possible on hand to assist a diagnosis. If the instant scanner has not performed enough scans to adequately support a diagnosis, the knowledge maintenance engine 70 ensures that adequate substitute data is available.

First, the knowledge maintenance engine 70 contains an acquisition protocol database 72. This database provides the modality and tracer specific information characteristic of the currently used acquisition protocol, as needed for the calibration of the physiological input data in conjunction with morphological input data. Often the analysis of the data will depend on the tracer that is used, so that information is provided so a filter 74 can select past scans that used the appropriate tracer or comparable tracers.

Another source of information available to the system is a control collective database 76. This database provides acquisition specific information needed to tell where and to what extent an individual patient data set significantly differs from the control collective. The control collective database 76 contains a sample of healthy subjects for comparison. This information is important for deciding whether a patient suffers from a disease indicated by variance of the patient's image to the control collective. If the patient's scan shows areas of hypo-intensity not in the control collective, then it is likely that further investigation is in order. Ideally, the control collective is comprised of images taken on the present scanner system; intensities, calibrations, artifacts, and the like are the same across the collective and present image data. Alternately, compensation algorithms can be constructed to normalize the control collective to the present images.

More specifically, the intensity of each voxel is compared with the corresponding voxel of one or more normal brain scans. Based on these comparisons, potentially weighted for regions of the brain that are more or less characteristic of dementia, the analysis 60 determines whether the patient is healthy, may be showing signs of dementia, etc. Further, the voxels which differ significantly from normal are used to generated the deviation pattern 64.

The system also includes a geometric reference database 78. This database defines a common geometric reference system of the control collective and the calibrated patient data. It contains all information for identifying and matching corresponding structures in the patient data and the control collective so that both data sets can be geometrically aligned as needed for the determination of the spatial distribution of deviation patterns between them. This component is specific to the geometrical arrangements of the data acquisition as well as the target application.

The knowledge maintenance engine 70 also contains a disease template database 80. This database contains disease and acquisition specific information needed to detect and classify the spatial distribution of the deviations from the control collective into characteristic patterns that allow for the scoring of different forms of dementia in the respective brain areas. For example, the disease template 80 includes a symptomatic collective or array of images that are characteristic of various dementia or dementia components. Again, the filter 74 can limit comparison studies from the control collective database 76, the geometric reference database 78 and the disease template database 80 to studies that are most relevant to the present subject. For example, only data using the same tracer, geometry, disease pattern, and the like could be used in analysis of the present scan.

The knowledge sources are properly selected and configured in light of the target, present application. This entails, for example, selecting the proper knowledge source from a predefined set of knowledge sources. This can be done automatically according to data retrieved from an electronic patient record or interactively by a technician performing the data acquisition. As the imaging process proceeds, the system can adjust for minor inconsistencies, requesting different subsets of information from the knowledge maintenance engine 70 based on, e.g., changes in the acquisition protocol, changes in the imaging equipment, etc. Changes and deviations among the knowledge sources that exceed certain safety margins can be signaled lest they jeopardize the quality of the final pattern classification and scoring. If appropriate, the system can update the knowledge maintenance engine 70 with the results of the present scan. This and other maintenance tasks can be performed by a quality control processor 82 ensuring internal consistency of the knowledge maintenance engine 70.

The knowledge maintenance engine 70 safeguards the result against malfunctions in the acquisition of the input images or changes in the patient clientele violating the validated application domain of the normal collectives. In this form, the system can also be used to control and supervise the accumulation of new knowledge sources as needed by specific forms of neurodegenerative diseases or new and more specific tracer substances. As such, it is a valuable tool not only for the early diagnosis of neurodegenerative diseases, but also for the development of their treatment by better and more specific drugs.

The comparison 66 of the deviation pattern 64 with the array of dementia characteristic patterns 80 results in a series of similarity/dissimilarity values or vectors. In one embodiment, the orientation/direction of these vectors is indicative of a dementia type and their magnitude is indicative of the degree of advancement of the dementia.

Once the analysis is complete, the system assigns a diagnosis score 84 (such as a feature vector) to the analyzed image. This provides the clinician with an estimate of the type of ailment. In the specific case of a brain scan, the system identifies the type of dementia that it is evident from the scans. The score can also reflect the probability, that is, the confidence that the indicated diagnosis is the correct diagnosis. The score can also reflect all of the various factors that play into the diagnosis, such as the areas affected, the degree of hypo-intensity, the extent of the hypo-intensity, and the like. It is preferable that the score, once provided to a clinician, can indicate an immediate estimate of the type and severity of the ailment.

Optionally, before any diagnosis takes place, images of the region of interest are produced using both modalities. Moreover, co-registered images can be produced by combining PET images of both PET and with images in which alignment points are clearly identifiable, such as MR, CT, or the like. Though PET and MRI represent substantially different techniques of image acquisition, which in no small part contributes to the complimentary nature of the two modalities, certain landmarks appear in both imaging modalities. By referencing these landmarks in the two images, the images can be co-registered into a representation with the advantages of both modalities by combining an inter-modality rigid registration with an automated MR landmark extraction. In the illustrated embodiment, the PET and MR images are collected concurrently or sequentially with scanning equipment with a known spatial relationship such that the PET and MR images are inherently aligned.

Figure 2:
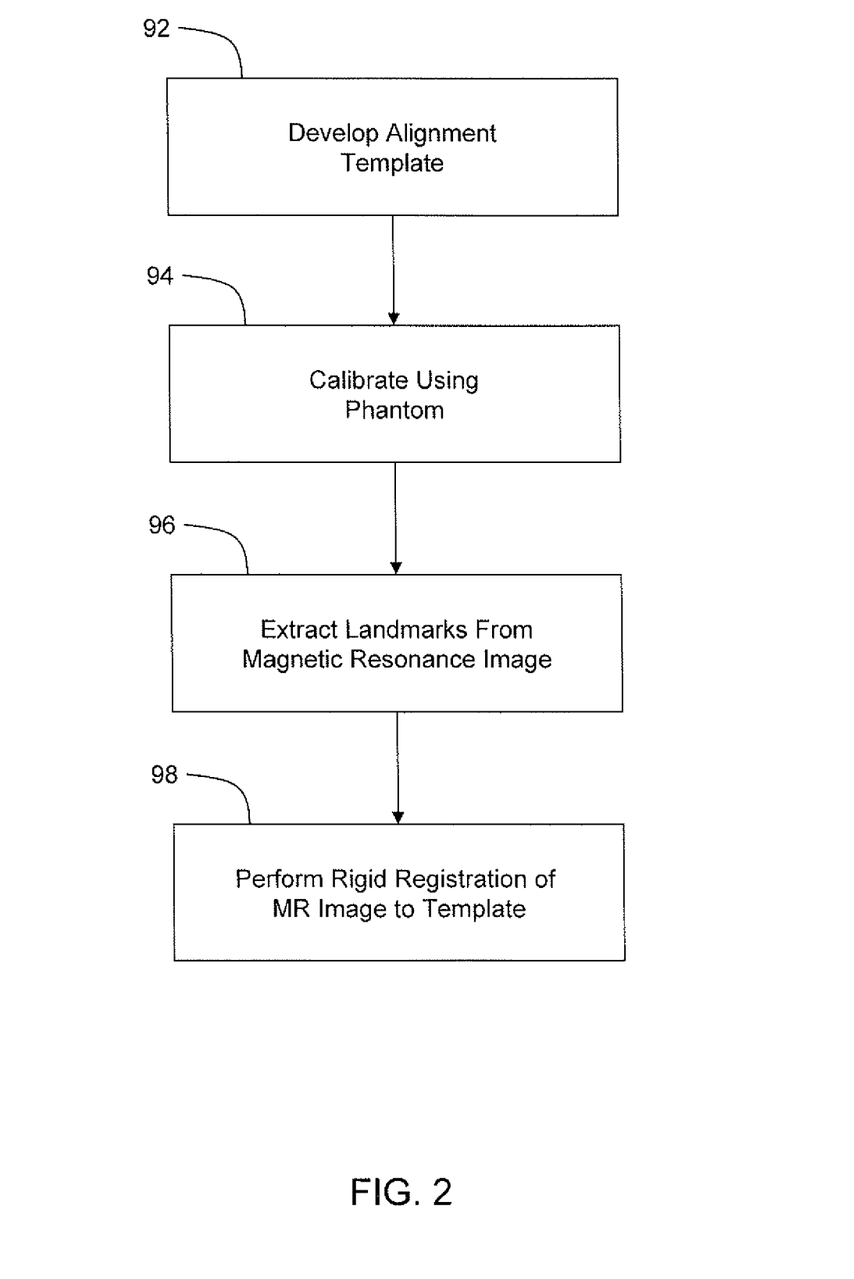
FIG. 2 is a flow diagram of an image registration process, in accordance with the present application.

The comparison of the patient image with the healthy brain images of the control collective 76 and the diseased images of the disease templates 80 is more accurate if the images are all scaled to the same size and if their brightness, intensity and other image properties are also normalized. A nominal skull size and orientation is developed and alignment points are selected. In the registration 90 corresponding points in the patient image are identified and the patient image is elastically transformed such that the alignment points of the patient image overlay the alignment points of the template. In one embodiment, the alignment points are only in the MR image and the intrinsically aligned PET image is transformed analogously. In another embodiment, some alignment points in the PET or SPECT image are used. The number of points can be only a few or can be very large. In one embodiment in the head, the bone is extracted forming an image of the skull and the transform is determined by aligning the two images. In other embodiments only selected points in the skull and or soft tissue are used to determine the transform. With reference to FIG. 2, an alignment template can be developed 92 by a known geometry, of a phantom 94, a normal sized patient skull, an average of prior images, or the like. The template has with markers or structures that are readily identifiable.

The mathematical transformation model and commonly matching target structures are provided by the template and the previously aligned atlas. Different forms of spatial alignment can be used, for example, a geometric brain model might be used to determine brain anatomy as derived from the MRI data, registration to the "average" tracer uptake pattern of a control collective, extraction of common anatomical landmarks clearly visible and unambiguously identifiable in the MRI and PET data, and the like.

The accurate definition of the landmarks in a high resolution MR image enables improved alignment of neuro (and other) images across subjects. In the particular case of a brain image, the local variation in the region of the selected structures is minimized Automatic landmark extraction 96 from an MR image is used to align a corresponding PET image of the same region of interest of the subject with the template. This generally includes two steps: estimation of the landmarks in the MR image and rigid registration 98 of the PET and the MR image with the template. The extraction of landmark positions in the MR image is preferably automated. Alternately, it can be performed manually by an imaging technician, but this is more time intensive. First, positions of a sparse set of landmarks are estimated in a set of characteristic two-dimensional planes. This can be done, for example, by implementing a SmartExam™ package available on MR consoles. Next, initial positioning of three-dimensional models of anatomical structures is performed. By using the landmarks previously obtained, the size and orientation of these structures (e.g. ventricle, cerebellum, and brain stem) can be placed. Next, the initial models are refined and adapted to match the position, orientation, and shape of the current subject's anatomy. Lastly, a set of anatomical landmarks is defined according to the final three-dimensional model positioning. These landmarks can also be points of the three-dimensional models themselves.

After the landmarks are identified in the MR image, they are identified in the PET image so the PET or both images can be aligned with the template. First, the landmarks are transformed from MR space into PET space by using the estimated rigid registration parameters. Given the positions of these landmarks in at least two PET images (e.g. the current subject's image and a template image derived from the control collective) these images can be aligned into a common space as follows. The positions of corresponding landmarks can be used to define a transformation for an arbitrary spatial location. For example, thin plate spline interpolation can be used. The interpolation enables image re-sampling such that one of the images can be re-sampled in alignment with the other image. Images so co-registered provide the benefits of both the MR and PET modalities to the clinician.

Figure 3:
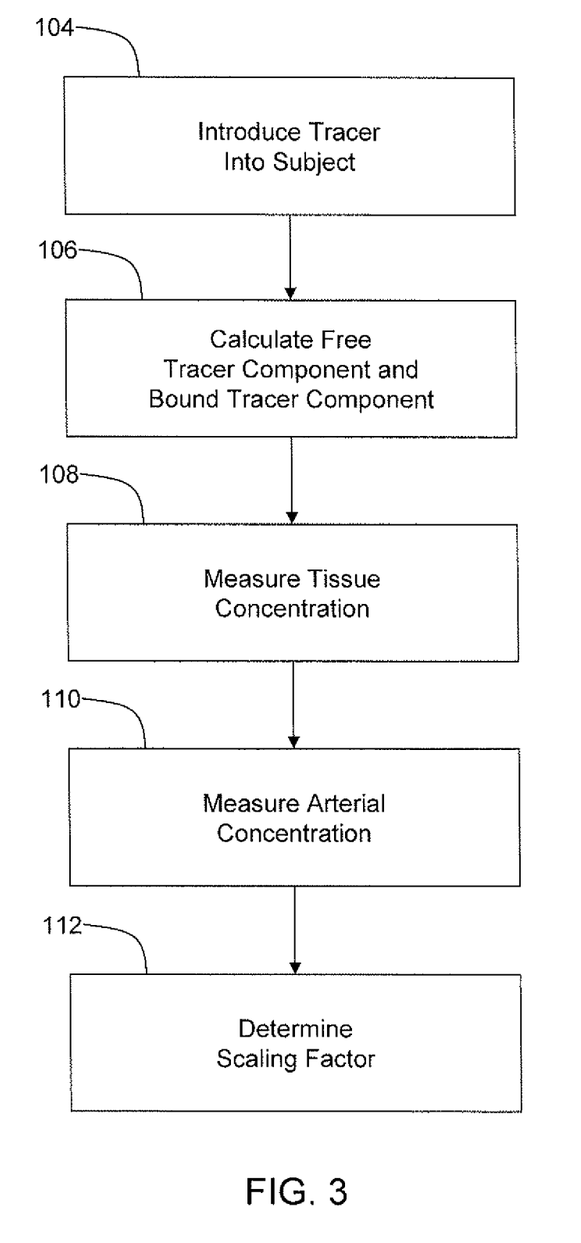
FIG. 3 is a flow diagram of a tracer uptake measurement, in accordance with the present application.

To ease and enhance co-registration of images, tracer uptake characteristics can be calculated. As mentioned previously, common methods of measuring blood flow to the brain include invasive, time consuming arterial sampling that provides significant discomfort to the patient. State of the art MR scanners can be configured to measure the inflow of blood to the brain via the carotid artery with a high degree of accuracy, and thus, an uptake processor 102 can calculate tracer uptake. With reference to FIG. 3, during a PET scan, a known volume of radioisotope tagged with a biological tracer is introduced into the patient 104. For brain imaging, glucose is a common tracer. By knowing the blood inflow into the brain, and the volume of radioisotope, the concentration of tracer arriving in the brain is directly calculable. Under the assumption that tracers are essentially trapped in the tissue with little or no washout, the imaged concentration can be divided into a free tracer component and an accumulating tracer component that represents the bound tracer 106. The Patlak model is an exemplary model for this calculation. Further, it is assumed that the free tracer component follows the general blood flow activity, with kinetics that are more rapid than the metabolic rate, such that the free tracer component approaches a constant B. Thus, a model of the two components can be expressed by the equation $$\frac{C_t(t)}{C_a(t)} = k_i \frac{\int_0^t C_a(\tau)d\tau}{C_a(t)} + B.$$

The tissue concentration $C_t(t)$ is measured 108 in relative terms in the PET image, and the arterial concentration $C_a(t)$ is measured 110 using MR flow estimation techniques, enabling estimation of the influx constant $k_i$. Resultantly, the absolute level of activity in the tissue is determined, and assuming that corresponding measurements are available for sets of reference or control images, the appropriate scaling factor can be determined 112. The uptake calculation has been described for measuring the uptake of tracer into the brain, but it is to be understood that uptakes in other regions of interest and/or using other tracer tags for the radioisotope have been contemplated. The application also finds use in SPECT. As available tracers and data acquisition geometries improve, SPECT imaging could potentially become as fast as PET, and would also allow for pharmacokinetic modeling.

Figure 4:
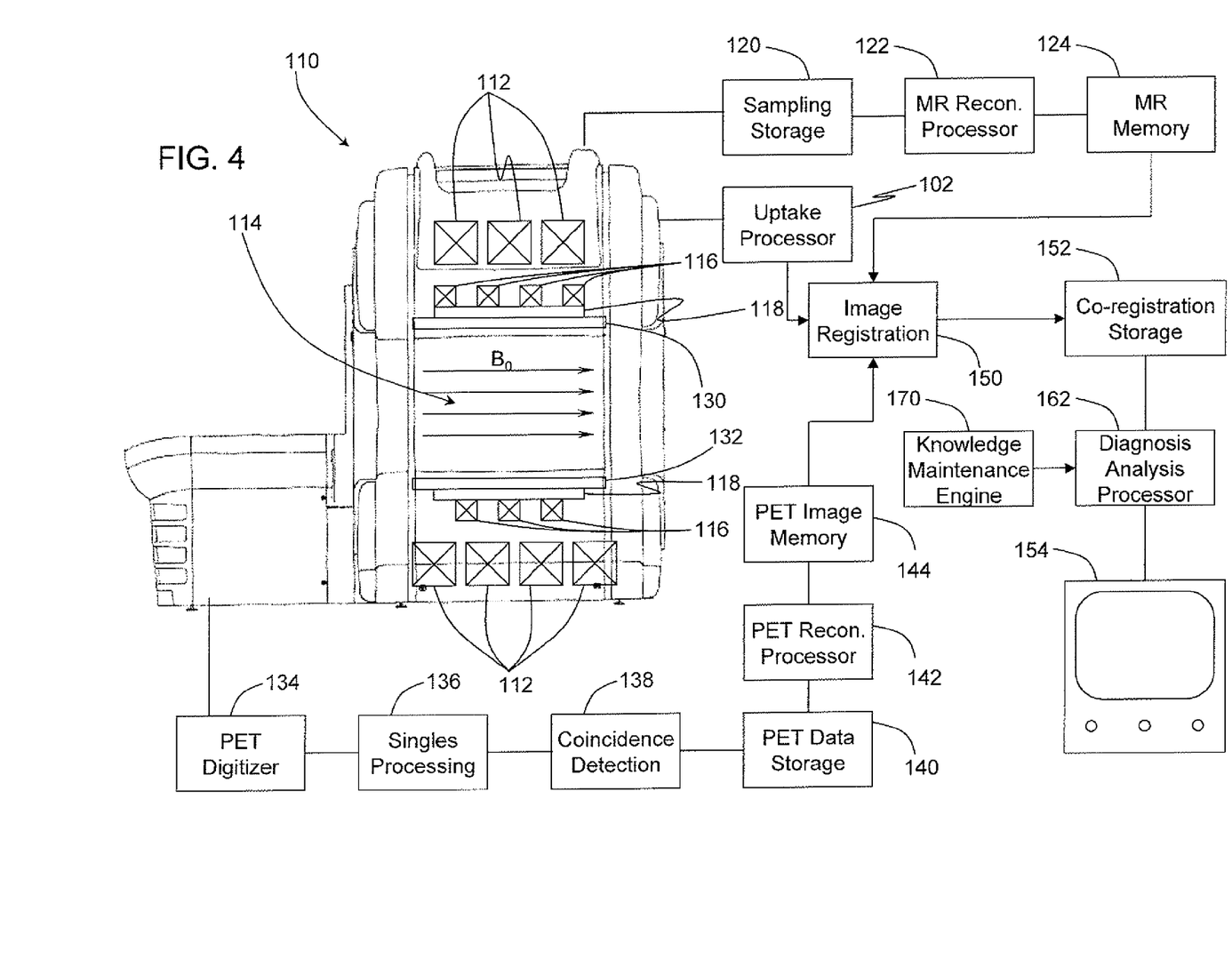
FIG. 4 is diagrammatic illustration of a combined PET/MR scanner, in accordance with the present application.

With reference to FIG. 4, an embodiment of a combined or hybrid magnetic resonance (MR) and PET data acquisition system 110, which generates intrinsically aligned PET and MR images. It is to be understood that a multimodality system is ideal for the sake of convenience; images taken from different scanners that are remotely located or spatially displaced are also contemplated, and similarly viable. The illustrated scanner 110 is a coplanar system, but other scanner orientations are equally plausible, such as side-by-side systems, insert systems, and the like. A magnetic resonance scanner includes a magnet 112 including a plurality of conductor coil windings (diagrammatically depicted in FIG. 4 by boxes with crossing lines) that generate a static magnetic field $B_0$ within an imaging region 114. The magnet 112 may be superconducting or resistive in nature; in the former case the magnet 112 is typically disposed in a cryogenic container or other cooling system (not shown). The illustrated magnet 112 is a solenoidal magnet having a relatively horizontal $B_0$ field through the imaging region 114. Though the polarity of the $B_o$ field is shown left to right, the opposite polarity is also suitable. In other embodiments, the magnet 112 may be otherwise oriented to produce a vertical or otherwise-oriented static magnetic field.

The magnetic resonance scanner also includes a magnetic field gradient assembly, which in the illustrative embodiment of FIG. 4 includes gradient coil windings 116 that cooperatively superimpose magnetic field gradients on the static $B_0$ magnetic field responsive to selective energizing of selected gradient coil windings 116. Optionally, the magnetic field gradient coil, magnet, or both may include other features not shown for forming, stabilizing, and dynamically adjusting the magnetic field, such as passive ferromagnetic shims, active shimming coils, and the like. The magnetic resonance scanner further includes a radio frequency excitation and reception system 118. The radio frequency system includes at least one component, such as the illustrated radio frequency coil 118, that can be energized at a suitable radio frequency to excite magnetic resonance in a subject disposed in the imaging region 114. The coil 118 can also operate as a radio frequency receiver to receive or detect magnetic resonance emanating from the imaging region 114 after RF excitation. In some embodiments, different coils are used for the excitation and reception operations. For example, the built-in coil 118 may be used to excite magnetic resonance, and a different, local coil (not shown) may be positioned over or close to the subject in the imaging region 114 to detect magnetic resonance. It is contemplated for the same magnetic resonance scanner to be configurable in different ways using different combinations of built-in coils, local coils, or both.

Received magnetic resonance samples are stored in a magnetic resonance sampling storage 120. A magnetic resonance reconstruction processor 122 applies a suitable reconstruction algorithm to reconstruct the magnetic resonance samples to form a reconstructed image that is stored in a magnetic resonance image memory 124. The reconstruction processor 122 applies a reconstruction algorithm that comports with the selected spatial encoding used in generating the magnetic resonance data. For example, a Fourier transform reconstruction algorithm may be suitable for reconstructing Cartesian-encoded magnetic resonance data.

With continuing reference to FIG. 4, the illustrated combined or hybrid MR and PET data acquisition system 110 further includes radiation detectors for performing PET data acquisition. In the illustrative example of FIG. 4, the radiation detectors include first and second arrays 130, 132 of radiation detectors. As will be described, each of the illustrated generally planar detector arrays 130, 132 includes a scintillator layer and a layer of electron multiplier-based photon detectors, however, other detector configurations such as a cylindrical detector array disposed about the imaging region 114 are contemplated. Solid state radiation detectors and solid state optical detectors are also contemplated. Each of the radiation detector arrays 130, 132 is configured to detect 511 keV gamma rays that are emitted by positron-electron annihilation events. In PET data acquisition, two substantially simultaneous 511 keV gamma ray detection events are presumed to have originated from the same positron-electron annihilation event, which is therefore located somewhere along a "line of response" (LOR) connecting the two substantially simultaneous 511 keV gamma ray detection events. This line of response is also sometimes called a projection or a ray, and the collected PET data is referred to as projection data.

In conventional PET, substantially simultaneous 511 keV gamma ray detection events are defined as two 511 keV gamma ray detection events occurring within a selected short time window, such as within one nanosecond of each other. Due to the variable annihilation position with respect to the detector elements a small (e.g., sub-nanosecond) time difference between the substantially simultaneous gamma photon detection events occurs. A related technique, called time-of-flight PET or TOF-PET, takes advantage of this small time difference to further localize the positron-electron annihilation event along the LOR.

The radiation detector arrays 130, 132 of the hybrid system 110 are used to acquire PET or TOF-PET data. The gamma ray detection events are processed by a PET digitization unit 134 that performs time-to-digital conversion (TDC) and analog-to-digital conversion (ADC) of detection events, and a singles processing unit 136 that performs clustering, energy estimation, timestamping, and positioning. The singles processing unit 136 optionally filters out detections that are outside of a selection energy window centered about on the expected 511 keV gamma ray energy. In some embodiments, the radiation detectors are pixelated, so that the spatial localization of the gamma ray detection events defining the projection correspond to a pixel size (i.e., physical size) of the radiation detectors of the radiation detector arrays 130, 132.

In other embodiments, clustering is applied by a block readout algorithm such as Anger logic or the like to provide further spatial localization refinement of the gamma ray detection events defining the projection. A coincidence detection processor 138 employs temporal windowing to identify gamma ray detection events that occurred substantially simultaneously, and hence likely correspond to a common positron-electron annihilation event and hence define a projection or line of response.

For TOF processing, the singles processing 136 and coincidence detection processing 138 can be swapped or interleaved so that the time difference between the identified substantially simultaneous or coincident detection events can be used to spatially localize the positron-electron annihilation event along the projection or line of response.

The resulting PET or TOF-PET data are stored in a PET data storage 140. A PET reconstruction processor 142 processes the projection or localized projection data using a suitable reconstruction algorithm to generate a reconstructed image that is stored in a PET images storage 144. For example, a filtered backprojection algorithm or iterative reconstruction algorithm can be employed. The system of FIG. 4 includes a discontinuous radiation detector array 130, 132 for PET that does not completely encircle the subject. The incomplete encirclement can lead to imaging artifacts due to "missing" projections or lines of response. For example, in the system of FIG. 4 no perfectly horizontal projections are collected, and so information ordinarily provided by such horizontal projections about vertical position is unavailable. Advantageously, if time-of-flight PET data are acquired and reconstructed then the time-of-flight localization provides additional information that compensates for the information that is lost by incomplete encirclement. As a qualitative example, the aforementioned missing information about vertical position can be compensated by a TOF-localized vertical projection, since the temporal localization of the electron-positron annihilation event along the vertical projection provides information about its vertical position.

The MR and PET acquisitions are optionally performed concurrently. Alternatively or additionally, MR and PET acquisition can be done sequentially (e.g., MR first followed by PET, or vice versa) or can be interleaved. An image registration processor 150 spatially registers and optionally temporally registers the reconstructed MR and PET images. If created, the co-registered images are stored in a co-registration image memory 152. The images so registered are suitably displayed on a display device 154, rendered using suitable two- or three-dimensional rendering software, or otherwise processed.

Although the system has been described in particular with respect to computer aided diagnosis of neurodegenerative diseases such as Alzheimer's dementia, it may also find application to the diagnosis of further neurological disorders, such as Parkinsonian disorders, which are also often diagnosed using functional imaging. It could also be applied to systematic processing or post-processing of medical datasets in other combinations of imaging modalities (for example, CT).

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of automated diagnosis comprising:
producing a first diagnostic image of a region of interest of a subject with a nuclear emission tomography scanner;
determining an amount of tracer uptake in the region of interest in a subject;
producing a second diagnostic image with a magnetic resonance scanner;
determining an amount of blood inflow into the region of interest with the magnetic resonance scanner;
aligning the first and second images;
consulting a knowledge maintenance engine for data from past imaging scans and diagnoses, the knowledge maintenance engine including an acquisition protocol database, a geometric reference database, a control collective database, and a disease templates database and a quality control processor that ensures internal consistency of the knowledge maintenance engine; and
analyzing the first diagnostic image, identifying areas of the first diagnostic image that appear different from images of an asymptomatic control collective.

2. The method as set forth in claim 1, wherein the step of consulting further includes:
applying a database filter to the knowledge maintenance engine to limit reference materials to ones relevant to a present study.

3. The method as set forth in claim 1, further including:
assigning a diagnostic feature vector to the first diagnostic image that indicates at least a diagnosis and a probability that the diagnosis is correct.

4. The method as set forth in claim 3, wherein the knowledge maintenance engine contains past diagnoses of dementia.

5. The method as set forth in claim 1, further including registering the first diagnostic image with the second diagnostic image, the registering including:
extracting landmarks from the first diagnostic image; and
aligning the first and second diagnostic images with a template using the extracted landmarks.

6. The method as set forth in claim 5, wherein the step of aligning further includes:
estimating a set of landmarks in a set of two dimensional planar slices of the region of interest.

7. The method as set forth in claim 6, further including:
aligning the first and second diagnostic images with the images of the asymptomatic control collective with the template using the extracted landmarks.

8. The method as set forth in claim 7, further including:
comparing at least the second image with the images of the asymptomatic control collective;
proposing a diagnosis based on the comparison.

9. The method as set forth in claim 8, wherein the images of the asymptomatic control collective includes images of other patients who have been diagnosed as healthy and images of other patients who have been diagnosed as diseased.

10. The method as set forth in claim 1, further including:
diagnosing a medical abnormality appearing in at least one of the first and second diagnostic images.

11. The method as set forth in claim 10, wherein the step of diagnosing further includes:
consulting a knowledge maintenance engine for data from past imaging scans and diagnoses;
analyzing the diagnostic images in light of the data from the knowledge maintenance engine; and
assigning a diagnosis score to the diagnostic images that indicates at least a diagnosis and a probability that the diagnosis is correct.

12. A method of automated diagnosis using a nuclear emission tomography scanner comprising:
producing a first diagnostic image of a region of interest of a subject;
aligning the first diagnostic image with a second diagnostic image by:
extracting landmarks from the second diagnostic image;
estimating a sparse set of landmarks in a set of two dimensional planar slices of the region of interest; and
determining an initial estimate of position for more detailed models of anatomical structures based on the landmarks, the step of positioning including:
adapting parameters of the models to anatomy of the subject; and
defining further landmarks based on a final positioning of the models in the subject's anatomy; and
consulting a knowledge maintenance engine for data from past imaging scans and diagnoses;
analyzing the registered first and second diagnostic image.

13. A method of automated diagnosis using a nuclear emission tomography scanner comprising:
introducing a radioisotope tagged with a tracer into the subject;
producing a first diagnostic image of a region of interest of the subject with a nuclear image tomography scanner, the first diagnostic image being indicative of an amount of tracer uptake in the region of interest of the subject;
producing a second diagnostic image of the region of interest with a magnetic resonance scanner;
from the second diagnostic image, determining an amount of blood inflow into the region of interest;
calculating an amount of tracer uptake in the region of interest; and
analyzing the first diagnostic image and the calculated tracer uptake and identifying areas of the first diagnostic image that appear different from images of an asymptomatic control collective.

14. The method as set forth in claim 13, wherein the step of calculating further includes:
determining an influx constant.

15. The method as set forth in claim 13, wherein the nuclear image tomography scanner is one of positron emission tomography and single photon emission computed tomography, which measures metabolic activity relative to the tracer in the region of interest.

16. The method as set forth in claim 13, wherein the analyzing includes, with a processor:
comparing the first diagnostic image with the images from the asymptomatic control collective to identify regions of abnormality;
comparing the tracer uptake in the regions of abnormality with a plurality of disease templates and determining a score indicative of similarity for each disease template;
from the scores, generating a diagnostic feature vector which indicates a diagnosis and a probability that the indicated diagnosis is correct.

17. The method as set forth in claim 13, further including:
determining a transform which brings landmarks identifiable in the second image into registration with corresponding landmarks in healthy and dementia image templates;
transforming the first diagnostic image with the transform;
comparing the transformed first diagnostic image with the healthy and dementia image templates.

18. The method as set forth in claim 13, further including:
consulting a knowledge maintenance engine for data from past imaging scans and diagnoses, the knowledge maintenance engine including an acquisition protocol database, a geometric reference database, a control collective database, and a disease templates database and a quality control processor that ensures internal consistency of the knowledge maintenance engine.

19. An apparatus for automated diagnosis using a nuclear emission tomography scanner, the apparatus comprising:
a processor programmed to:
align a nuclear emission first diagnostic image with an anatomical second diagnostic image of the region of interest by performing the steps of:
extracting landmarks from the second diagnostic image;
estimating a set of landmarks in a set of two dimensional planar slices of the region of interest; and
determining an initial estimate of position for more detailed models of anatomical structures based on the landmarks, the step of positioning including:
adapting parameters of the models to anatomy of the subject; and
defining further landmarks based on a final positioning of the models in the subject's anatomy;
consult a knowledge maintenance engine of data from past imaging scans and diagnoses, the knowledge maintenance engine including an acquisition protocol database, a geometric reference database, a control collective database, and a disease templates database and a quality control processor that ensures internal consistency of the knowledge maintenance engine; and
analyze a first diagnostic image of a region of interest of a subject produced by the nuclear emission tomography scanner to identify areas of the first diagnostic image that appear different from images of an asymptomatic control collective.

20. The apparatus as set forth in claim 19, wherein the processor is further programmed to:
compare the first diagnostic image with the images from the asymptomatic control collective to identify regions of abnormality;
compare uptake in the regions of abnormality with a plurality of disease templates and determining a score indicative of similarity for each disease template;
from the scores, generate a diagnostic feature vector which indicates a diagnosis and a probability that the indicated diagnosis is correct.

21. The apparatus as set forth in claim 19, wherein the processor is further programmed to:
determine a transform which brings landmarks identifiable in a the second diagnostic image of the region of interest into registration with corresponding landmarks in healthy and dementia image templates;
transform the first diagnostic image with the transform;
compare the transformed first diagnostic image with the healthy and dementia image templates.

22. An apparatus for automated diagnosis using a nuclear emission tomography scanner, the apparatus including, a processor programmed to:
produce a first diagnostic image of a region of interest;
align the first diagnostic image with a second diagnostic image by:
extracting landmarks from the second diagnostic image;
estimating a sparse set of landmarks in a set of two dimensional planar slices of the region of interest; and
determining an initial estimate of position for more detailed models of anatomical structures based on the landmarks, the step of positioning including:
adapting parameters of the models to anatomy of the subject; and
defining further landmarks based on a final positioning of the models in the subject's anatomy; and
consult a knowledge maintenance engine for data from past imaging scans and diagnoses;
analyze the registered first and second diagnostic image.

* * * * *